United States Patent [19]
Martin

[11] 3,941,826
[45] Mar. 2, 1976

[54] (CYANO-DIALKYLPHENYL) ALKYL SULFIDES, SULFOXIDES AND SULFONES

[75] Inventor: Elmore Louis Martin, Wilmington, Del.

[73] Assignee: E. I. Du Pont de Nemours and Company, Wilmington, Del.

[22] Filed: Feb. 24, 1975

[21] Appl. No.: 552,034

Related U.S. Application Data

[62] Division of Ser. No. 394,825, Sept. 6, 1973, Pat. No. 3,879,472.

[52] U.S. Cl.................. 260/465 R; 71/98; 71/103
[51] Int. Cl.² ................................. C07C 121/52
[58] Field of Search .............................. 260/465 R

[56] References Cited
UNITED STATES PATENTS
2,900,409  8/1959  Heininger et al. ............... 260/465

*Primary Examiner*—Lewis Gotts
*Assistant Examiner*—Dolph H. Torrence

[57] ABSTRACT

Compounds having the structure:

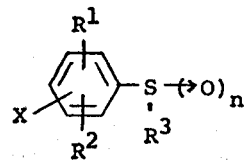

wherein
- $R^1$ and $R^2$, alike or different, are alkyls of 2 to 7 carbon atoms in which there are no more than 3 carbon atoms in a line from the aromatic ring;
- $R^3$ is an alkyl of 1 to 3 carbon atoms;
- $n$ is 0, 1 or 2; and
- X is F, Cl, Br, I, or CN;

with the provisos that
1. $R^1$ and $R^2$ are not ortho to each other,
2. at least one of $R^1$ and $R^2$ contains at least 3 carbon atoms, and
3. X is not ortho to the

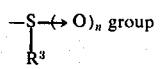

group have been found to be selective herbicides.

6 Claims, No Drawings

(CYANO-DIALKYLPHENYL) ALKYL SULFIDES, SULFOXIDES AND SULFONES

CROSS-REFERENCE TO RELATED APPLICATION

This is a division of copending application Ser. No. 394,825, filed Sept. 6, 1973, now U.S. Pat. No. 3,879,472.

BACKGROUND OF THE INVENTION

1. Field of the Invention

This invention relates to (substituted dialkylphenyl) alkyl sulfides, sulfoxides and sulfones in which the dialkylphenyl group is additionally substituted with fluorine, chlorine, bromine, iodine or cyano, and to their use as selective herbicides.

2. Description of the Prior Art

Belgian Patent No. 776,357 (1970) discloses phenyl alkyl sulfones and sulfoxides of the formula:

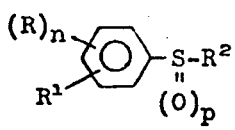

in which $n = 1$ or 2;
$p = 1$ or 2;
when $n = 1$, R is alkyl or alkoxy of 1 to 3 carbons;
when $n = 2$, the two R's may be alkyl or alkoxy of 1 to 3 carbons, chlorine, or (together) may form an $-O-(CH_2)_m-O-$ group where $m$ is 1, 2 or 3;
$R^1$ is H or, when at least one R group is alkoxy, $R^1$ may also be Cl, Br, alkyl or alkoxy of 1–3 to 3 carbons, $NO_2$, and amino (including salts);
$R^2$ is alkyl of 1 to 7 carbons, alkenyl or alkynyl of 3 to 5 carbons, or hydroxyalkyl of 2 to 3 carbons.

The products are said to be useful in the treatment of cardiovascular disorders.

U.S. Pat. No. 3,140,226, issued July 7, 1964, discloses compounds toxic to microorganisms and having the structure:

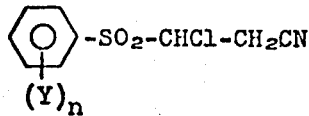

where Y = F, Cl, Br, I or alkyl of 1 to 6 carbons, and $n = 0-5$.

SUMMARY OF THE INVENTION

This invention comprises compounds having the structure:

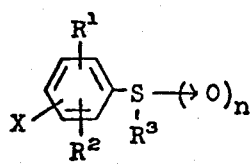

wherein
$R^1$ and $R^{2}$, alike or different, are alkyl of 2 to 7 carbon atoms in which there are no more than 3 carbon atoms in a line from the aromatic ring;
$R^3$ is an alkyl of 1 to 3 carbon atoms;
$n$ is 0, 1 or 2; and
X is F, Cl, Br, I or CN;
with the provisos that
1. $R^1$ and $R^2$ are not ortho to each other,
2. at least one of $R^1$ and $R^2$ contains at least three carbon atoms and
3. X is not ortho to the

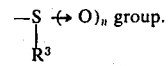 group.

DETAILED DESCRIPTION OF THE INVENTION

1. Preparation of the Compounds

The compounds of this invention are made by a suitable sequence of standard reactions that are generally known to those skilled in the art. The requirement that $R^1$ and $R^2$ of the general formula cannot be ortho to each other should be kept in mind with the understanding that such undesired isomers must be avoided or separated from the isomers sought.

A suitable reaction sequence could begin with the preparation of a dialkylbenzene from an alkylbenzene by the well-known procedure:

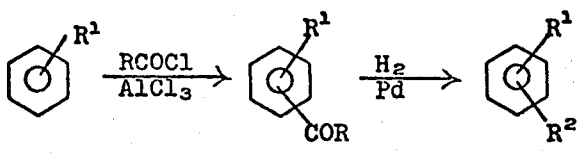

Bromine and chlorine-substituted dialkylbenzenes can be made by standard halogenation procedures, i.e.,

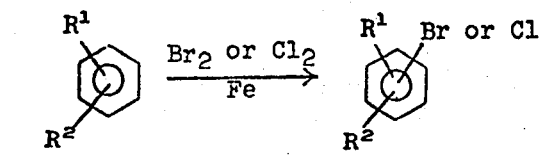

as described by H. Suzuki et al. in Bull. Chem. Soc. (Japan), 39, p. 128 (1866).

The halobenzenes of Table I were prepared by brominating or chlorinating the corresponding dialkylbenzene following the procedure of A. Newton, Jour. Am. Chem. Soc., 65, p. 2441 (1943) for the bromination of p-di-isopropylbenzene.

TABLE I

| Compound | bp °C/mm |
|---|---|
| 2,5-Diisopropylbromobenzene | 79–84/0.6 |
| 2,5-Di-sec-butylbromobenzene | 94–98/0.15 |
| 5-sec-Butyl-2-isopropylbromobenzene | 71–75/0.08 |
| 2,5-Diisopropylchlorobenzene | 70–73/0.6 |
| 2-Isobutyl-5-isopropylchlorobenzene | 62/0.1 |

Iodine-substituted dialkylbenzenes can be prepared by iodination in the presence of $HIO_4$, sulfuric acid and acetic acid as described in Org. Syn., 51, p. 94 (1971).

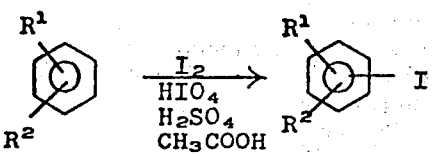

The fluorine-substituted dialkylbenzenes can be made by the Schiemann reaction on a dialkylaniline, prepared from a bromodialkylbenzene, by reaction with ammonia (Org. Syn., 28, p. 22, 1948), in accordance with the equations:

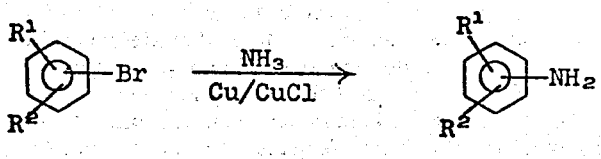

and

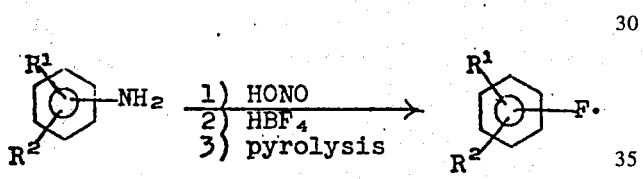

Sulfonyl chlorides are then prepared from the halogen-substituted dialkylbenzene by well-known chlorosulfonation procedures, i.e.,

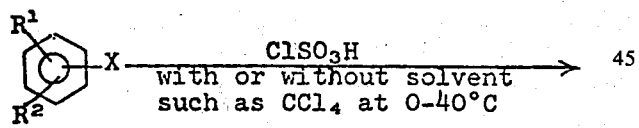

Usually 3 to 4 equivalents of ClSO$_3$ are used.

Thiophenols can be prepared by reduction of the sulfonyl chlorides using common reducing agents, such as lithium aluminum hydride (LAH) or Zn/H$_2$SO$_4$, i.e.,

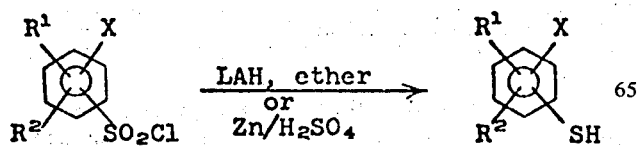

The lithium aluminum hyride reduction is carried out with three equivalents of lithium aluminum hydride in ether or tetrahydrofuran and gives the thiophenol cleanly in high yields, but is somewhat more costly than the zinc reduction.

Halogen-substituted dialkylphenyl alkyl sulfides may be prepared from the thiophenols by reaction of a salt of the thiophenol (e.g., Na or K) with an alkylating agent such as R$^3$-Y, where Y = Cl, Br, I; or (R$^3$)$_2$SO$_4$ in accordance with the equation:

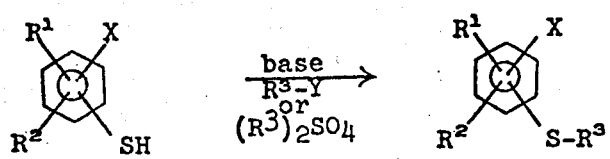

The halogen-substituted dialkylphenyl alkyl sulfoxides and sulfones are prepared by oxidation of the sulfides using common procedures, i.e.,

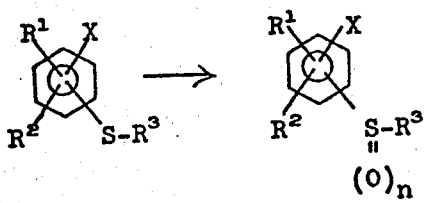

where $n = 1$ or 2

| Oxidant | product |
|---|---|
| NaIO$_4$, H$_2$O$_2$, etc. | n = 1 |
| H$_2$O$_2$, peracids, etc. | n = 2 |

Other oxidizing agents can also be employed as described in "Organic Functional Group Preparations" by S. R. Sandler and W. Karo, Academic Press, 1968, Chs. 19 and 20.

The cyano substituent may be introduced by substitution of cyano for chlorine, bromine or iodine by means of the Rosemund von Braun reaction, i.e.,

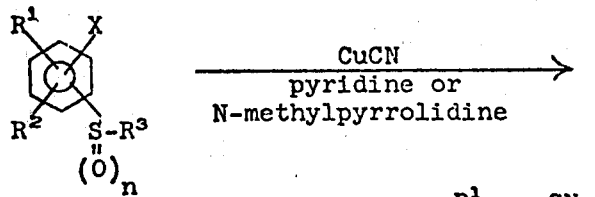

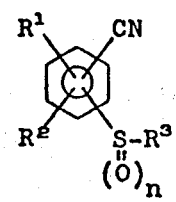

as described by L. Friedman & H. Shechter in Jour. Org. Chem., 26, p. 2522 (1961); and M. S. Newman and H. Boden in Jour. Org. Chem., 26, p. 2525 (1961).

2. Utility of the Compounds

The compounds of this invention have varied herbicidal activities, that is, they differ according to structure with regard to pre- and post-emergence activity, grassy versus broadleaved plant response, as well as varied responses between species. They are primarily useful as preemergence herbicides at rates of application of about 0.4–10 lbs per acre (0.45–11 kg/hectare), but some also show postemergence activity. By proper selection of structure and rate of application, one can provide selective weed control in such crops as soybeans, wheat, green and dry beans, rice and cotton.

Useful formulations of the compounds of this invention can be prepared in conventional ways. These include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1-99% by weight of active ingredient and at least one of (a) about 0.1–20% surfactant and (b) about 1–99% solid or liquid diluent. More specifically, they will contain these ingredients in the following approximate proportions.

TABLE II

|  | Active Ingredient | Diluent(s) | Surfactant(s) |
| --- | --- | --- | --- |
| Wettable powders | 20–90 | 0–74 | 1–10 |
| Oil suspensions, emulsions, solutions (including emulsifiable concentrates) | 5–50 | 40–95 | 0–15 |
| Aqueous suspensions | 10–50 | 40–84 | 1–20 |
| Dusts | 1–25 | 70–99 | 0–5 |
| Granules and pellets | 1–95 | 5–99 | 0–15 |
| High-strength compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Suitable solid diluents are those described in Watkins et al., "Handbook of Insecticide Dust Diluents and Carriers", 2nd Ed., Dorland Books, Caldwell, N.J. The more absorptive diluents are preferred for wettable powders and the denser ones for dusts. Suitable liquid diluents and solvents are those described in Marsden, "Solvents Guide", 2nd Ed., Interscience, New York, 1950. Solubility under 0.1% is preferred for suspension concentrates; solution concentrates are preferably stable against phase separation at 0°C. suitable surfactants include those described in "McCutcheon's Detergents and Emulsifiers Annual", Allured Publ. Corp., Ridgewood, N.J., as well as Sisely and Wood, "Encyclopedia of Surface Active Agents", Chemical Publishing Co., Inc. New York, 1964. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet-milling as described by Littler in U.S. Pat. No. 3,060,084. Granules and pellets may be made by spraying the active material upon preformed granular carriers or by agglomeration techniques as described by J. E. Browning in "Agglomeration", Chemical Engineer's Handbook, 4th Ed., McGraw-Hill, New York, 1963, pp. 8–59ff.

EXAMPLES OF THE INVENTION

The following examples, illustrating the novel products of this invention and their use as herbicides, are given without any intention that the invention be limited thereto. All percentages are by weight unless otherwise specified.

EXAMPLE 1

4-Bromo-2,5-diisopropylphenyl Methyl Sulfide

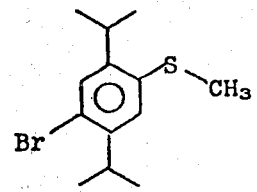

A. 4-Bromo-2,5-diisopropylbenzene sulfonyl chloride was prepared as follows: Chlorosulfonic acid, 154 g, was added over 15 minutes to 80 g of 2,5-diisopropylbromobenzene in 200 ml of carbon tetrachloride. The reactants were stirred for 30 minutes longer and then poured onto a mixture of ice and saturated sodium chloride solution. The organic layer was washed with cold water and dried over magnesium sulfate. Removal of the solvent gave 105 g of crystalline product. Recrystallization from n-hexane gave pure 4-bromo-2,5-diisopropylbenzene sulfonyl chloride, which softened at 77°C and melted at 80.5°–83°C.

B. 4-Bromo-2,5-diisopropylbenzenethiol

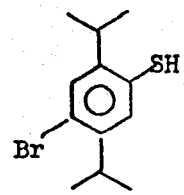

was prepared as follows

A solution of 110.3 g of 4-bromo-2,5-diisopropylbenzenesulfonyl chloride in 500 ml of ether was added dropwise over 2 hours to 34.2 g of lithium aluminum hydride suspended in 300 ml of ether. The reactants were then refluxed for 16 hours. Hydrochloric acid, 10%, was added with cooling until by-product salts precipitated. The reaction mixture was filtered and the filtrate dried over sodium sulfate. Removal of the solvent gave 78.4 g of pale-yellow crystalline product which was recrystallized from n-hexane to give pure 4-bromo-2,5-diisopropylbenzenethiol having a melting point of 72°–75°C.

C. 4-Bromo-2,5-diisopropylphenyl methyl sulfide was prepared as follows

A mixture of 78.4 g of 4-bromo-2,5-diisopropylbenzenethiol and 12.8 g of sodium hydroxide was stirred together in 200 ml of water while 50.4 g of dimethylsulfate was added at a rate to maintain the reaction temperature between 45°–55°C. After stirring for 3 hours at ambient temperature, the reaction mixture was extracted with ether. The ether solution, washed with half saturated sodium chloride solution and dried over sodium sulfate, was concentrated to an oil which was distilled to give 64 g of 4-bromo-2,5-diisopropylphenyl methyl sulfide, boiling at 91°–93°C at 0.15–0.1 mm Hg; $N_D^{23}$ 1.5714.

D. 4-Bromo-2,5-diisopropylphenyl methyl sulfide in preemergence application at 2 lb/acre (2.25 kg/hectare) effected complete control of crabgrass, sorghum and wild oats and strong growth retardation of barnyard grass, radish, dock and rice. No effect was observed on nutsedge, cassia, mustard, beans, soybeans or wheat. In post-emergence application at 2 and 10 lb/acre (2.25 and 11 kg/hectare), test plants were slightly burned.

EXAMPLE 2

4-Bromo-2,5-di-sec-butylphenylmethyl Sulfide

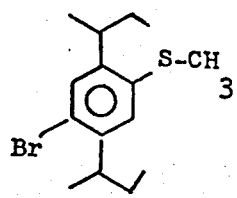

A. 4-Bromo-2,5-di-sec-butylbenzenesulfonyl chloride was prepared by the procedure of Example 1 A. except that 2,5-di-sec-butylbromobenzene was substituted for 2,5-diisopropylbromobenzene. The resulting product had a boiling point of 148°C. at 0.15 mm Hg.

B. 4-Bromo-2,5-di-sec-butylbenzenethiol

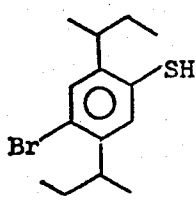

was prepared as follows

A 128-ml portion of concentrated sulfuric acid was added to 300 g of ice while keeping the temperature at 0°–10°C. Then 41 g of 4-bromo-2,5-di-sec-butylbenzenesulfonyl chloride was added. While maintaining the temperature at 0°–10°C, 65 g of zinc dust was added with good agitation over a period of 2 hours. The reaction mixture was then heated under reflux on a steam bath for 5 hours. After cooling, the mixture was extracted into methylene dichloride, dried over magnesium sulfate, filtered, and concentrated to an oil which was distilled, to give 27 g of 4-bromo-2,5-di-sec-butylbenzenethiol, bp 106°–107°C/0.22 mm, $n_D^{25}$ 1.5599.

C. 4-Bromo-2,5-di-sec-butylphenyl methyl sulfide was prepared using the procedure of Example 1C except that 4-bromo-2,5-di-sec-butylbenzenethiol was substituted for the 4-bromo-2,5-diisopropylbenzenethiol. The resulting product had a boiling point of 126°C at 0.3 mm Hg.

EXAMPLE 3

4-Chloro-2,5-diisopropylphenyl methyl sulfide

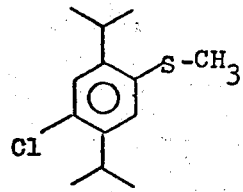

A. 4-Chloro-2,5-diisopropylbenzenesulfonyl chloride was prepared by the procedure of Example 1A except that 2,5-diisopropylchlorobenzene was substituted for the 2,5-diisopropylbromobenzene.

B. 4-Chloro-2,5-diisopropylbenzenethiol was prepared by the procedure of Example 2B except that 4-chloro-2,5-diisopropylbenzenesulfonyl chloride was substituted for the 4-bromo-2,5-di-sec-butylbenzenesulfonyl chloride. The resulting product had a boiling point of 93°–95°C at 0.3 mm Hg.

C. 4-Chloro-2,5-diisopropylphenyl methyl sulfide was prepared using the procedure of Example 1C except that 4-chloro-2,5-diisopropylbenzenethiol was substituted for the 4-bromo-2,5-diisopropylbenzenethiol. The resulting product had a boiling point of 88°C at 0.35 mm Hg.

D. 4-Chloro-2,5-diisopropylphenyl methyl sulfide in preemergence application at 0.4 lb/acre (0.45 kg/hectare) effected slight to moderate retardation of crabgrass, barnyard grass, sorghum, wild oats, corn and wheat, but otherwise was inactive. Increase of the application to 2 lb/acre (2.25 kg/hectare) completely inhibited emergence of sorghum, wild oats and wheat and strongly stunted barnyard grass and corn. There was no activity in post emergence application at this level.

Post emergent application of 4-chloro-2,5-diisopropylphenyl methyl sulfide at a rate of 10 lb/acre (11kg/hectare) effected 60–90% chlorosis (loss of chlorophyll) on Johnson grass, barnyard grass and crabgrass. This compound also effected 100% control of nutsedge in preemergence application. Corn was also extensively stunted, but soybean and rice were not affected.

EXAMPLE 4 4-Bromo-2,5-diisopropylphenyl Isopropyl Sulfide

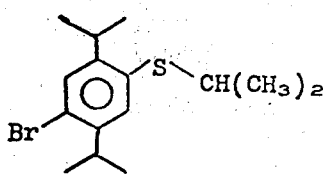

A 54.6-g portion of 4-bromo-2,5-diisopropylbenzenethiol prepared in Example 1B was added to a solution of 4.8 g of sodium dissolved in 200 ml of ethanol. Isopropylbromide, 36.9 g, was added dropwise to the above solution under nitrogen. The reactants were refluxed for 7 hours and then poured into 500 ml of water. After acidification with 10% HCl, the oily product was extracted into ether which was washed in turn with water and saturated sodium chloride solution. Drying over sodium sulfate and solvent removal gave 62.8 g of 4-bromo-2,5-diisopropyl isopropyl sulfide as a pale-yellow oil of high purity.

EXAMPLE 5

4-Bromo-2,5-diisopropylphenyl n-propyl sulfide

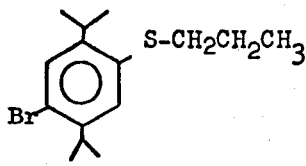

4-Bromo-2,5-diisopropylphenyl n-propyl sulfide was prepared using the procedure of Example 4 except that n-propylbromide was substituted for isopropylbromide.

EXAMPLE 6

4-Bromo-2-sec-butyl-5-isopropylphenyl methyl sulfide

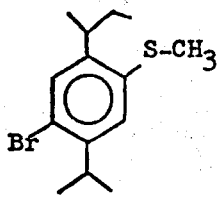

A. 4-Bromo-2-sec-butyl-5-isopropylbenzenesulfonyl chloride was prepared using the procedure of Example 1A except that 2-sec-butyl-5-isopropylbromobenzene was substituted for the 2,5-diisopropylbromobenzene. The resulting product had a boiling point of 128°–130°C at 0.08 mm Hg.

B. 4-Bromo-2-sec-butyl-5-isopropylbenzenethiol was prepared using the procedure of Example 2B except that 4-bromo-2-sec-butyl-5-isopropylbenzenesulfonyl chloride was substituted for the 4-bromo-2,5-di-sec-butylbenzenesulfonyl chloride. The resulting product had a boiling point of 110°C at 0.35 mm Hg.

C. 4-Bromo-2-sec-butyl-5-isopropylphenyl methyl sulfide was prepared using the procedure of Example 1C except that 4-bromo-2-sec-butyl-5-isopropylbenzenethiol was substituted for the 4-bromo-2,5-diisopropylbenzenethiol. The resulting product had a boiling point of 111°C at 0.3 mm Hg.

EXAMPLE 7

4-Chloro-2-isopropyl-5-isobutylphenyl methyl sulfide

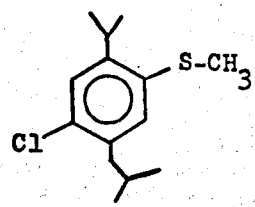

A. 4-Chloro-2-isopropyl-5-isobutylbenzenesulfonyl chloride was prepared using the procedure of Example 1A except that 2-isopropyl-5-isobutylchlorobenzene was substituted for the 2,5-diisopropylbromobenzene. The resulting product had a melting point of 90°–94°C.

B. 4-Chloro-2-isopropyl-5-isobutylbenzenethiol was prepared using the procedure of Example 2B except that 4-chloro-2-isopropyl-5-isobutylbenzenesulfonyl chloride was substituted for the 4-bromo-2,5-di-sec-butylbenzenesulfonyl chloride. The resulting product had a boiling point of 77°C at 0.1 mm Hg.

C. 4-Chloro-2-isopropyl-5-isobutylphenyl methyl sulfide was prepared using the procedure of Example 1C except that 4-chloro-2-isopropyl-5-isobutylbenzenethiol was substituted for the 4-bromo-2,5-diisopropylbenzenethiol. The resulting product had a boiling point of 89°C at 0.08 mm Hg.

EXAMPLE 8

4-Cyano-2,5-diisopropylphenyl methyl sulfide

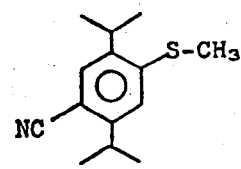

A. 4-Cyano-2,5-diisopropylphenyl methyl sulfide was prepared as follows: A mixture of 20.4 g of 4-bromo-2,5-diisopropylphenyl methyl sulfide prepared as in Example 1C and 8.9 g of cuprous cyanide was heated at reflux in 100 ml of N-methylpyrrolidone under nitrogen for 2 hours. After cooling to ambient temperature, the reaction mixture was poured into a mixture of 200 ml of water and 100 ml of concentrated aqueous ammonia. The product was filtered and extracted into ether. The extract was washed with 5% HCl followed by a saturated solution of sodium chloride. The organic layer was dried over sodium sulfate and the solvent removed to give 15.5 g of 4-cyano-2,5-diisopropyl methyl sulfide which was recrystallized from n-hexane giving pure product having a melting point of 72°–75°C.

Anal. Calcd. for $C_{14}H_{19}NS$: C, 72.05; H, 8.21; N, 6.00;

Found: C, 72.17; H, 8.05; N, 6.05.

B. 4-Cyano-2,5-diisopropylphenyl methyl sulfide in preemergence application at 0.4 lb/acre (0.45 kg/hectare) exhibited no activity toward nutsedge, cassia, mustard, dock, or soybeans, but completely prevented emergence of crabgrass, barnyard grass, sorghum, wild oats and wheat and strongly stunted the growth of morning glory, dock and rice. Post-emergence application had no effect at 0.4 lb/acre (0.45 kg/hectare) crabgrass was moderately stunted.

EXAMPLE 9

4-Bromo-2,5-diisopropylphenyl methyl sulfoxide

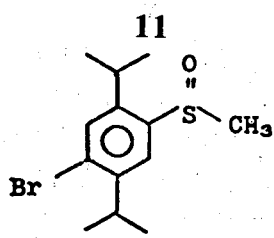

A. 4-Bromo-2,5-diisopropylphenyl methyl sulfoxide was prepared as follows: A solution of 25.7 g of sodium m-periodate in 200 ml of water was added portionwise over 0.5 hour to 31.9 g of 4-bromo-2,5-diisopropylphenyl methyl sulfide (prepared in Example 1C) in 200 ml of methanol and 350 ml of acetone at ambient temperature. After stirring for 16 hours, the reaction mixture was filtered and the solid portion was extracted with chloroform. The filtrate was diluted with 1 liter of water and the solid residue that formed was collected on a filter. The second residue was extracted with chloroform. The two chloroform extracts were combined, washed with half-saturated sodium chloride solution, and dried over sodium sulfate. Removal of the chloroform gave a pale-yellow product containing some sulfide which was removed by recrystallization from n-hexane to give pure 4-bromo-2,5-diisopropylphenyl methyl sulfoxide which softened at 110°C and melted at 114°–117°C [Y(S=O) 9.6μ].

B. 4-Bromo-2,5-diisopropylphenyl methyl sulfoxide prepared in Part A above in preemergence application at 0.4 lb/acre (0.45 kg/hectare) inhibited growth of all test plants except nutsedge, cassia and marigold. Small to moderate adverse effects were observed on beans, corn and wheat. Post emergency application at 0.4 lb/acre (0.45 kg/hectare) showed slight burn on beans and moderate burn on nutsedge. A 2 lb/acre (2.25 kg/hectare) extensive hormone effect was observed on Johnson grass and crabgrass; cotton, Johnson grass and crabgrass were burned.

EXAMPLE 10

4-Bromo-2,5-diisopropylphenyl methyl sulfone

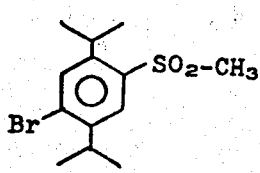

A. 4-Bromo-2,5-diisopropylphenyl methyl sulfone was prepared as follows. A 55-g portion of 30% hydrogen peroxide was added to a solution of 28.7 g of 4-bromo-2,5-diisopropylphenyl methyl sulfide (prepared in Example 1C) in 100 ml of acetic acid over a period of 25 min. while maintaining the temperature at 50°–60°C. The reaction mixture was then refluxed at 90°C for 4 hrs., after which time it was poured into cold water. The product was filtered and washed with water to give 23.1 g of 4-bromo-2,5-diisopropylphenyl methyl sulfone. After recrystallization from 75% ethanol water the 4-bromo-2,5-diisopropylphenyl methyl sulfone melted at 107°–112°C.

B. 4-Bromo-2,5-diisopropylphenyl methyl sulfone in preemergence application at 0.4 lb/acre (2.45 kg/hectare) strongly inhibited growth or completely prevented emergence of barnyard grass, sorghum, wild oats, morning glory, mustard radish, dock, rice and wheat, but showed little or no activity against crabgrass, nutsedge, cassia, marigold, beans or soybeans. In post emergence application, no activity was noted at 0.4 lb/acre (0.45 kg/hectare) while at 2 lb/acre (2.25 kg/hectare) this compound showed severe retardation of crabgrass.

EXAMPLE 11

4-Chloro-2,5-diisopropylphenyl methyl sulfone

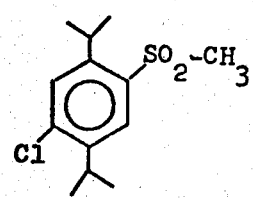

A. 4-Chloro-2,5-diisopropylphenyl methyl sulfone was prepared using the procedure of Example 10A except that 4-chloro-2,5-diisopropylphenyl methyl sulfide was substituted for the 4-bromo-2,5-diisopropylphenyl methyl sulfide. The resulting product had a boiling point of 127°C at 0.25 mm Hg.

B. 4-Chloro-2,5-diisopropylphenyl methyl sulfone at 2 lb/acre (2.25 kg/hectare) in preemergence application was 60–90% effective in controlling the growth of sorghum, wild oats, cassia, mustard and morning glory. Emergence of crabgrass, barnyard grass and dock was completely inhibited. In post-emergence activity at 2 lb/acre (2.25 kg/hectare) it was effective in stunting the growth of cotton and crabgrass and in chlorosis of barnyard grass.

4-Chloro-2,5-diisopropylphenyl methyl sulfone showed very specific activity in preemergence application at 0.4 lb/acre (0.45 kg/hectare). The compound was inert toward radish, marigold, beans, and only slightly stunted growth of soybeans and rice and caused slight chlorosis of corn. Wheat had hormonal injury. Crabgrass, sorghum and wild oats were severely stunted, and barnyard grass was 100% inhibited.

EXAMPLE 12

4-Bromo-2,5-diisopropylphenyl isopropyl sulfone

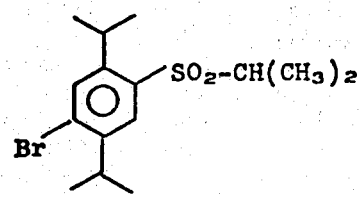

4-Bromo-2,5-diisopropylphenyl isopropyl sulfone was prepared as follows: A solution of 9.15 g of m-chloroperbenzoic acid (85%) in 925 ml of methylene dichloride was added dropwise to an ice-cooled solution of 62.8 g of 4-bromo-2,5-diisopropylphenyl isopropyl sulfide (prepared in Example 4) in 200 ml of methylene dichloride at a rate to maintain the temperature between 10° and 25°C. The reactants were then stirred at ambient temperature for 17 hours. The reaction mixture was filtered and the filtrate washed in turn with 10% sodium bicarbonate solution and water. After drying over sodium sulfate and solvent removal there remained 73.6 g of a white solid which was recrystalllized from n-hexane and then methanol to give 4-bromo-2,5-diisopropylphenyl isopropyl sulfone, which softened at 77°C and melted at 85°–93°C.

EXAMPLE 13

4-Bromo-2,5-diisopropylphenyl n-propyl sulfone

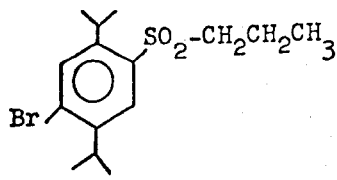

A. 4-Bromo-2,5-diisopropylphenyl n-propyl sulfone was prepared following the procedure of Example 12 except that 4-bromo-2,5-diisopropylphenyl n-propyl sulfide was substituted for 4-bromo-2,5-diisopropylphenyl isopropyl sulfide.

B. 4-Bromo-2,5-diisopropylphenyl propyl sulfone was inactive at 0.4 lb/acre (0.45 kg/hectare) preemergence application except for considerable stunting of barnyard grass and some stunting of wild oats. At the level of 2 lb/acre (2.25 kg/hectare) activity was somewhat increased and in post-emergence application at 2 lb/acre (2.25 kg/hectare) slight chlorosis of Johnson grass, crabgrass and barnyard grass was observed.

EXAMPLE 14

4-Cyano-2,5-diisopropylphenyl Methyl Sulfone

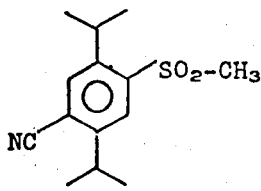

A. A mixture of 4-bromo-2,5-diisopropylphenyl methyl sulfone (19.9 g) prepared in Example 10A and 7.2 g of cuprous cyanide was heated in 100 ml of N-methyl pyrrolidone at 195°C under nitrogen for 2 hours. The reaction mixture was poured into a stirred solution of 25 g of ethylenediamine in 500 ml of water. The mixture was filtered and the residual product extracted into tetrahydrofuran. The extract was washed with 5% HCl and finally with saturated sodium chloride solution. After drying over magnesium sulfate, the solvent was removed to give 4-cyano-2,5-diisopropylphenyl methyl sulfone. Further purification by recrystallization from n-hexane gave 4-cyano-2,5-diisopropylphenyl methyl sulfone having a mp of 134°–137°C.

Anal. Calcd. for $C_{14}H_{19}NO_2S$: C, 63.36; H, 7.22; N, 5.28;

Found: C, 63.30; H, 7.53; N, 5.39.

B. 4-Cyano-2,5-diisopropylphenyl methyl sulfone in preemergence application at 0.4 lb/acre (0.45 kg/hectare effected complete inhibition of emergence of crabgrass, sorghum, rice, wheat and barnyard grass and strong stunting of wild oats, nutsedge, cassia, morning glory, mustard, radish and dock. Corn was chlorotic and soybeans showed some chlorosis. This compound was inert in post-emergence application at 0.4 lb/acre (0.45 kg/hectare and at 2 lb/acre (2.25 kg/hectare) showed mild chlorosis of Johnson grass, crabgrass and barnyard grass.

EXAMPLE 15

4-Bromo-2,5-di-sec-butylphenyl methyl sulfone

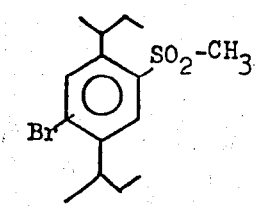

4-Bromo-2,5-di-sec-butylphenyl methyl sulfone was prepared using the procedure of Example 10A excpept that 4-bromo-2,5-di-sec-butylphenyl methyl sulfide was substituted for the 4-bromo-2,5-diisopropylphenyl methyl sulfide. The resulting product had a boiling point of 146°C at 0.3 mm Hg.

EXAMPLE 16

4-Bromo-5-sec-butyl-2-isopropylphenyl methyl sulfone

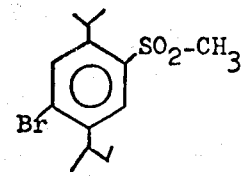

4-Bromo-5-sec-butyl-2-isopropylphenyl methyl sulfone was prepared using the procedure of Example 10A, except that 4-bromo-5-sec-butyl-2-isopropylphenyl methyl sulfide was substituted for the 4-bromo-2,5-diisopropylphenyl methyl sulfide. The product had a boiling point of 148°C at 0.4 mm Hg.

EXAMPLE 17

4-Chloro-2-isopropyl-5-isobutylphenyl methyl sulfone

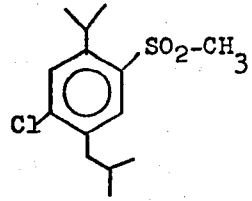

4-Chloro-2-isopropyl-5-isobutylphenyl methyl sulfone was prepared using the procedure of Example 10A except that 4-chloro-2-isopropyl-5-isobutylphenyl methyl sulfide was substituted for the 4-bromo-2,5-diisopropylphenyl methyl sulfide. The resulting product had a boiling point of 130°–135°C at 0.13 mm Hg.

EXAMPLE 18

4-Cyano-2,5-di-sec-butylphenyl methyl sulfone

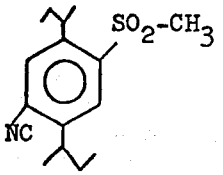

A. 4-Cyano-2,5-di-sec-butylphenyl methyl sulfone was prepared using the procedure of Example 8A except that 4-bromo-2,5-di-sec-butylphenyl methyl sulfone was substituted for the 4-bromo-2,5--diisopropylphenyl methyl sulfone. The product had a boiling point of 158°C at 0.3 mm Hg.

B. 4-Cyano-2,5-di-sec-butylphenyl methyl sulfone in preemergence application at 0.4 lb/acre (0.45 kg/hectare controlled the growth of crabgrass, barnyard grass, sorghum, wild oats and effected moderate control of morning glory and dock. Corn was also stunted but beans, soybeans, rice and wheat were not affected. In post-emergence application at 2 lb/acre (2.25 kg/hectare), barnyard grass was strongly stunted and crabgrass moderately stunted. Barnyard grass and nutsedge were unaffected at 0.4 lb/acre (0.45 kg/hectare).

EXAMPLE 19

4-Cyano-2-sec-butyl-5-isopropylphenyl methyl sulfone

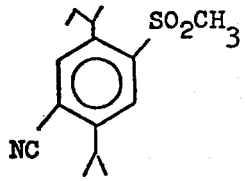

A. 4-Cyano-2-sec-butyl-5-isopropylphenyl methyl sulfone was prepared using the procedure of Example 8A except that 4-bromo-2-sec-butyl-5-isopropylphenyl methyl sulfone was substituted for the 4-bromo-2,5-diisopropylphenyl methyl sulfone. The product had a boiling point of 165°C at 0.35 mm Hg.

B. 4-Cyano-2-sec-butyl-5-isopropylphenyl methyl sulfone prepared above in preemergence application at 0.4 lb/acre (0.45 kg/hectare) effected complete control of crabgrass, barnyard grass, wild oats and dock, and showed 50–90% retardation of growth of sorghum, nutsedge, cassia, morning glory, mustard, radish and marigold. Beans, corn, soybeans and rice were severely stunted and wheat showed adverse hormonal effects. At 2 lb/acre (2.25 kg/hectare) all test plants were severely stunted or emergence completely prevented. At 2 lb/acre (2.25 kg/hectare post-emergence application. Johnson grass showed extensive malformation and crabgrass was severely stunted.

EXAMPLE 20

4-Cyano-2,5-diisopropylphenyl n-propyl sulfone

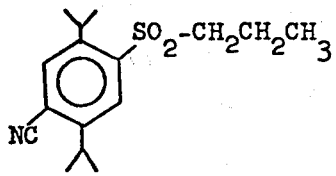

A. 4-Cyano-2,5-diisopropylphenyl n-propyl sulfone was prepared using the procedure of Example 8A except that 4-bromo-2,5-diisopropylphenyl n-propyl sulfone was substituted for the 4-bromo-2,5-diisopropylphenyl methyl sulfone. The product had a melting point of 113°–115°C.

B. 4-Cyano-2,5-diisopropylphenyl propyl sulfone (prepared above) showed specific activity in preemergence application at 0.4 lb/acre (0.45 kg/hectare) in causing severe growth retardation of barnyard grass and inactivity toward food crops (beans, corn, soybeans, rice and wheat). At 2 lb/acre (2.25 kg/hectare) application this compound additionally showed slight to moderate stunting of sorghum, wild oats, morning glory, marigold, dock and corn. There was essentially no activity in post-emergence.

EXAMPLE 21

4-Cyano-2,5-diisopropylphenyl isopropyl sulfone

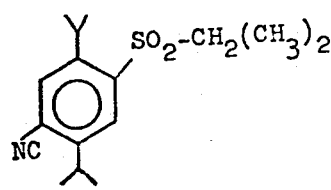

A. 4-Cyano-2,5-diisopropylphenyl isopropyl sulfone was prepared using the procedure of Example 8A except that 4-bromo-2,5-diisopropylphenyl isopropyl sulfone was substituted for the 4-bromo-2,5-diisopropylphenyl methyl sulfone. The product softened at 126°C and melted at 130°–134°C.

B. 4-Cyano-2,5-diisopropylphenyl isopropyl sulfone prepared above was inactive at 0.4 lb/acre (0.45 kg/hectare) and at 2 lb/acre (2.25 kg/hectare) except for stunting crabgrass, Johnson grass, sorghum at the latter rate of application. Emergence of nutsedge was completely prevented.

Although the invention has been described and exemplified by way of specific embodiments, it is not intended that it be limited thereto. As will be apparent to those skilled in the art, numerous modifications and variations of these embodiments can be made without departing from the spirit of the invention or the scope of the following claims.

I claim:

1. The compounds having the structure

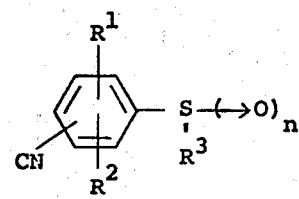

wherein
$R^1$ and $R^2$, alike or different, are alkyl of 2 to 7 carbon atoms in which there are no more than 3 carbons in a line from the aromatic ring;
$R^3$ is an alkyl of 1 to 3 carbon atoms; and
$n$ is 0, 1 or 2
with the provisos that:
1. $R^1$ and $R^2$ are not ortho to each other,
2. at least one of $R^1$ and $R^2$ contains at least 3 carbon atoms, and
3. CN is not ortho to the

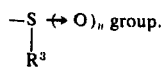
2. The compound of claim 1 wherein $R^1$ and $R^2$ are of 3 to 4 carbon atoms, $R^3$ is methyl and $n = 2$.
3. The compound of claim 1, 4-cyano-2,5-diisopropylphenyl methyl sulfide.
4. The compound of claim 1, 4-cyano-2,5-diisopropylphenyl methyl sulfone.
5. The compound of claim 1, 4-cyano-2-sec-butyl-5-isopropylphenyl methyl sulfone.
6. The compound of claim 1, 4-cyano-2,5-di-sec-butylphenyl methyl sulfone.
\* \* \* \* \*